United States Patent [19]

Phillips

[11] Patent Number: 4,673,395
[45] Date of Patent: Jun. 16, 1987

[54] DUAL BARREL INJECTOR

[75] Inventor: Ian R. Phillips, Killara, Australia

[73] Assignee: N.J. Phillips Pty. Limited, New South Wales, Australia

[21] Appl. No.: 843,090

[22] Filed: Mar. 24, 1986

[30] Foreign Application Priority Data

Mar. 26, 1985 [AU] Australia .............................. PG9903

[51] Int. Cl.⁴ ............................................. A61M 5/08
[52] U.S. Cl. .................................................. 604/191
[58] Field of Search ............... 604/191, 207, 208, 209, 604/218; 222/135, 136, 137, 386

[56] References Cited

U.S. PATENT DOCUMENTS 1,948,388  2/1934  Liberson .............................. 604/191
4,403,989  9/1983  Christensen et al. ................ 604/191

Primary Examiner—John D. Yasko
Attorney, Agent, or Firm—Ladas & Parry

[57] ABSTRACT

A multi dose injector having a pair of interacting pistons and cylinders enabling the delivery of two different liquids into an animal upon the single operation of a trigger.

10 Claims, 2 Drawing Figures

DUAL BARREL INJECTOR

The present invention relates to drench guns or syringes for the dosing of animals and, in particular, to a dual barrel injector.

Drench guns have been conventionally provided with variable dose adjustment mechanisms. However, these known drench guns can only deliver a single dose at each operation.

There is a need to provide a multi dose injector whereby with a single operation an animal may be injected with two or more liquids, and more particularly a multi dose injector which may be adjusted to vary the dose delivered in respect of each liquid.

It is the object of the present invention to overcome or substantially ameliorate the above disadvantages.

There is disclosed herein a multi dose injector for injecting liquids, said injector comprising: a body, a plurality of cylinders mounted on the body and each having an associated piston, with each cylinder and its associated piston co-operating to define a variable volume working spacing, an outlet passage extending from each space enabling the passage of liquid therefrom upon relative movement between each cylinder and its associated piston to decrease the volume of the space defined thereby, an inlet passage extending to each space enabling the delivery of liquid to each space upon relative movement between each piston and its associated cylinder to increase the volume of the space defined thereby, operator manipulable means to cause relative movement between each cylinder and its associated piston to vary the volume of the space defined thereby, and valve means restricting the liquid to pass from the inlet passages to the outlet passages during operation of the injector.

There is further disclosed herein a multi dose injector for injecting liquids, said injector comprising a body, a plurality of cylinders mounted on the body and each having an associated piston, with each piston and its associated cylinder co-operating to define a variable volume working space, an outlet passage extending from each space enabling the passage of liquid therefrom upon relative movement between each piston and its associated cylinder to decrease the volume of the space defined thereby, an inlet passage extending to each space enabling the delivery of liquid to each space upon relative movement between each piston and its associated cylinder to increase the volume of the space defined thereby, operator manipulable means to cause relative movement between each piston and its associated cylinder to vary the volume of the space defined thereby, the adjustment means enabling the volume of at least one space to be adjusted relative to the other space/s in order to adjust the volume of the dose delivered by said one space relative to the other space/s.

A preferred form of the present invention will now be described by way of example with reference to the accompanying drawings, wherein.

Figure 1:
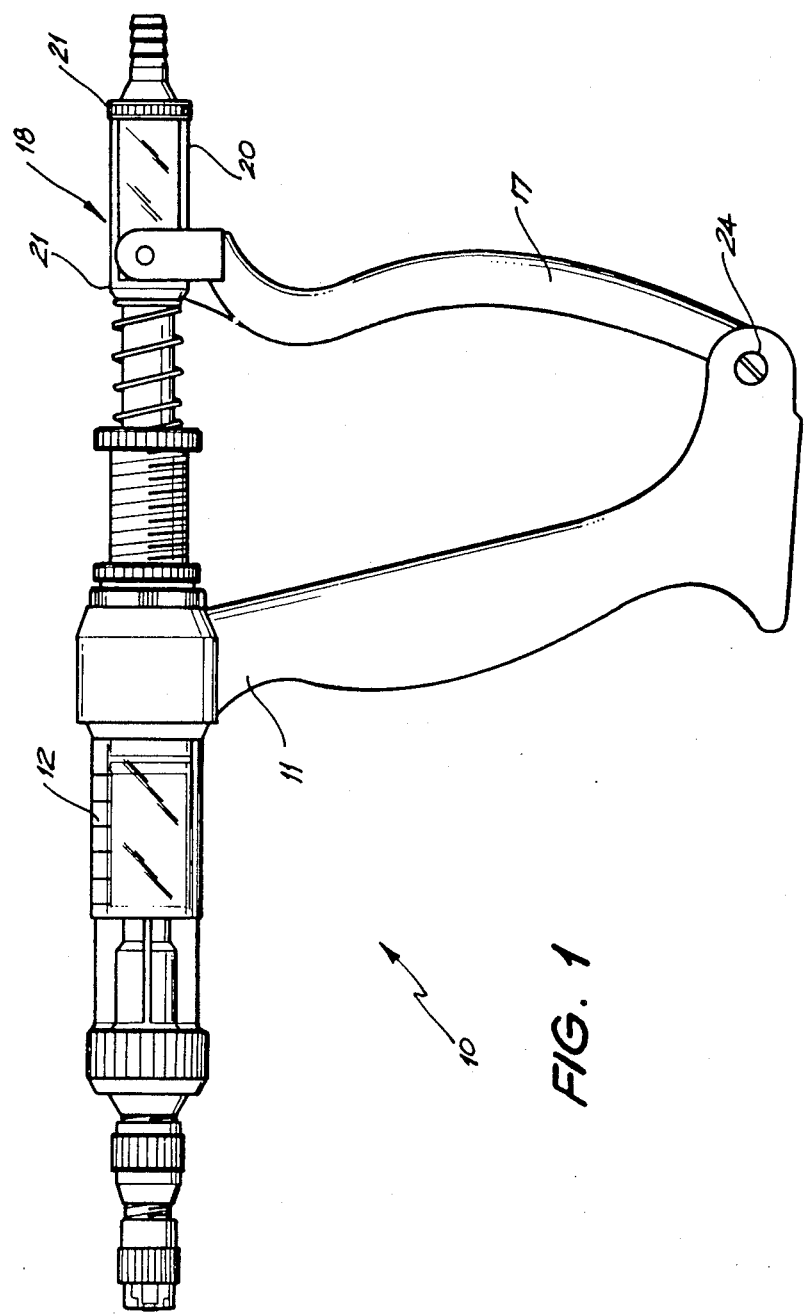
FIG. 1 is a schematic side elevation of a drench gun or syringe.
Figure 2:
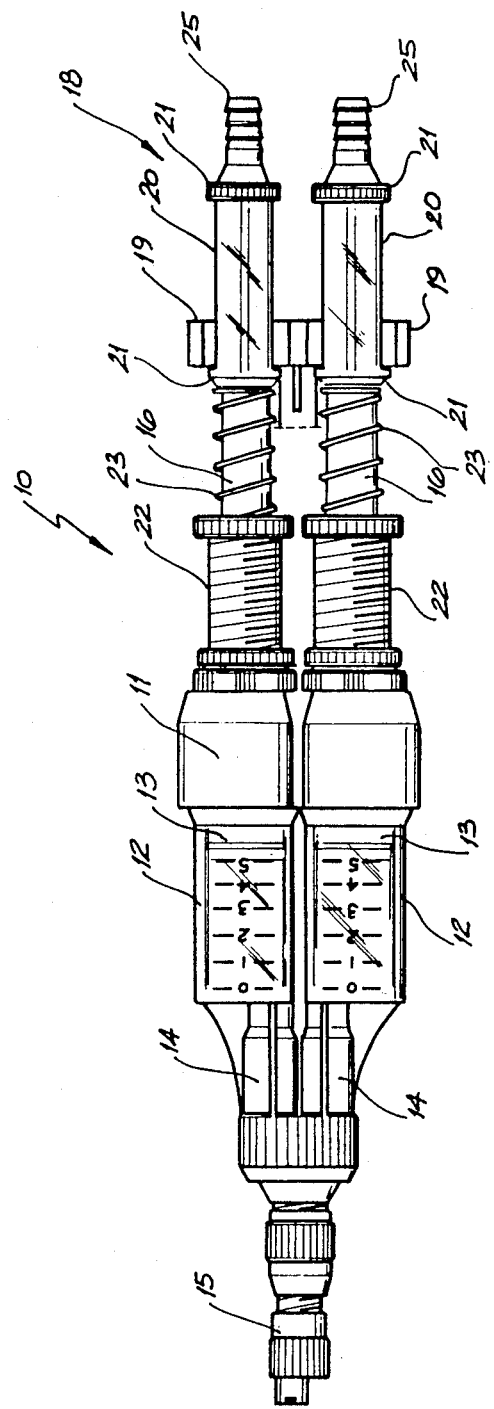
FIG. 2 is a schematic plan view of the drench gun or syringe of FIG. 1.

In FIGS. 1 and 2 there is schematically depicted a drench gun or syringe 10. The syringe or gun 10 is provided with a body 11 supporting two cylinders 12. Slidably located within each cylinder 12 is a piston 13 with each piston 13 co-operating with its associated cylinder 12 to define a variable volume working space. Extending from each cylinder 12 is an outlet passage 14 which lead to an injector needle mounting or nozzle mounting 15.

Extending from each piston 13 is a piston rod 16 which is coupled to a trigger 17 by means of a lost motion assembly 18. The lost motion assembly 18 includes two yokes 19 which slidably engage enlarged portions 20 formed on each piston rod 16. The enlarged portions 20 are defined at each end by flanges 21. The yokes 19 are slidable relative to the enlarged portions 20 with the sliding motion having limits defined by the flanges 21.

Slidably surrounding each piston rod 16 is a dose adjustment sleeve 22 with each adjustment sleeve 22 threadably engaging the body 11 and having one extremity located within the cylinders 12 so as to abut the rear end of its associated pistons 13. By rotation of the adjustment sleeves 22, the rest positions of the pistons 13 is predetermined to thereby predetermine the volume of the next dose delivered. It should be appreciated that the piston rods 16 are slidable through the sleeves 21 and the body 11 to thereby enable operation of the pistons 13. The pistons 13 are resiliently biased to a position maximising the volumes defined within the cylinders 12, by springs 23. The springs 23 abut the ends of the adjustment sleeves 22 and the flanges 21 to thereby bias the piston rods 16 rightward as seen in FIG. 2.

The trigger 17 is pivotally attached to the body 11 by means of a pin 24 and, accordingly, the syringe or gun 10 is operated by the operator placing a handle around the body 11 and the trigger 17 and causing movement of the trigger 17 in a pivoting motion towards the body 11.

It should further be appreciated that the piston rods 16 are provided with a passage which also extends through the pistons 13. The ends of the piston rods 16 are provided with barbed portions 25 to enable the gun or syringe 10 to be attached via flexible tubing to reservoirs of the liquids to be injected into the animals.

By providing the syringe or gun 10 with a lost motion assembly 18, the doses delivered by each piston may be independently adjusted. If one dose is adjusted so as to be smaller, one of the yokes will not engage its associated flange 22, when in the rest position.

The abovedescribed embodiment has the pistons 13 mounted for movement relative to the cylinders 12, in the respect it should be noted that the only requirement is that there is relative movement between the pistons 13 and the associated cylinders 12. Accordingly the pistons could be held stationary and the cylinders move relative thereto.

If so required the number of cylinders and pistons could be increased.

What I claim is:

1. A multi dose injector for injecting liquids, comprising a body, a plurality of cylinders mounted on the body and each having an associated piston, with each cylinder and its associated piston co-operating to define a variable volume working space, an outlet passage extending from each space enabling the passage of liquid therefrom upon relative movement between each cylinder and its associated piston to decrease the volume of the space defined thereby, an inlet passage extending to each space enabling the delivery of liquid to each space upon relative movement between each piston and its associated cylinder to increase the volume of the space defined thereby, operator manipulable means to cause simultaneous relative movement between each cylinder and its associated piston to vary the volume of the spaces defined thereby, value means restricting the liquid to pass from the inlet passages to the outlet passages during operation of the injector, and wherein said outlet passages extend to a common outlet so that upon the simultaneous decrease in volume of the spaces, the liquids contained therein are simultaneously moved through said common outlet.

2. The injector of claim 1 wherein said cylinders are mounted on said body so as to be fixed relative thereto, and said operator manipulable means includes a trigger pivotably mounted on said body and engaging said pistons to cause movement thereof relative to the cylinders.

3. The injector of claim 2 further including a piston rod extending from each piston and wherein the inlet passage of each respective cylinder extends through the associated piston and its piston rod.

4. The injector of claim 3 further including adjustment means enabling the volume of at least one of said spaces to be adjusted relative to the other spaces.

5. The injector of claim 4 wherein said adjustment means includes a lost motion assembly allowing selected independent movement of at least one of the piston rods relative to the other piston rod/s.

6. The injector of claim 5 wherein said adjustment means further includes an adjustably movable abuttment to selectively limit the movement of at least one piston in order to adjust the volume of said space defined thereby.

7. A multi dose injector for injecting liquid, said injector comprising a body, a plurality of cylinders mounted on the body and each having an associated piston, with each piston and its associated cylinder co-operating to define a variable volume working space, an outlet passage extending from each space enabling the passage of liquid therefrom upon relative movement between each piston and its associated cylinder to decrease the volume of the space defined thereby, an inlet passage extending to each space enabling the delivery of liquid to each space upon relative movement between said piston and its associated cylinder to increase the volume of the space defined thereby, operator manipulable means to cause relative movement between each piston and its associated cylinder to vary the volume of the space defined thereby, and adjustment means enabling the volume of at least one space to be adjusted relative to the other space/s in order to adjust the volume of the dose delivered by said one space relative to the other space/s.

8. The injector of claim 7 wherein said adjustment means includes an adjustable abuttment to limit the travel of the piston defining said one space.

9. The injector of claim 8 further including a piston rod extending from each cylinder and a lost motion assembly coupling the piston rods to said operator manipulable means to allow limited relative movements between the pison rods.

10. The multi dose injector of claim 1 wherein said outlet passages extend to a common outlet so that upon the simultaneous decrease in volume of said spaces, said liquids are moved through said common outlet.

* * * * *